United States Patent
Löffler et al.

(10) Patent No.: US 7,025,973 B2
(45) Date of Patent: *Apr. 11, 2006

(54) ACID COSMETIC, DERMATOLOGICAL AND PHARMACEUTICAL AGENTS

(75) Inventors: Matthias Löffler, Niedernhausen (DE); Roman Morschhäuser, Mainz (DE)

(73) Assignee: Clariant GmbH, Frankfurt (DE)

( * ) Notice: Subject to any disclaimer, the term of this patent is extended or adjusted under 35 U.S.C. 154(b) by 101 days.

This patent is subject to a terminal disclaimer.

(21) Appl. No.: 10/433,204

(22) PCT Filed: Nov. 28, 2001

(86) PCT No.: PCT/EP01/13861

§ 371 (c)(1),
(2), (4) Date: Nov. 17, 2003

(87) PCT Pub. No.: WO02/43686

PCT Pub. Date: Jun. 6, 2002

(65) Prior Publication Data

US 2004/0115148 A1 Jun. 17, 2004

(30) Foreign Application Priority Data

Dec. 1, 2000 (DE) .............................. 100 59 822

(51) Int. Cl.
*A61K 9/08* (2006.01)
*A61K 9/10* (2006.01)
*A61K 9/107* (2006.01)
*A61K 7/075* (2006.01)
*A61K 47/32* (2006.01)

(52) U.S. Cl. ................ 424/400; 424/70.16; 424/70.22; 514/937; 514/975

(58) Field of Classification Search .. 424/70.16–70.18, 424/400, 422, 70.12, 70.22–70.28, 78.18; 514/937–38, 942, 975
See application file for complete search history.

(56) References Cited

U.S. PATENT DOCUMENTS

| 5,104,645 | A | | 4/1992 | Cardin et al. ................. 424/70 |
|---|---|---|---|---|
| 5,736,125 | A | | 4/1998 | Morawsky et al. ........... 424/59 |
| 5,981,615 | A | * | 11/1999 | Meijs et al. ................. 522/137 |
| 6,054,138 | A | | 4/2000 | Trebosc et al. .............. 424/401 |
| 6,120,780 | A | | 9/2000 | Dupuis et al. ............... 424/401 |
| 6,123,960 | A | | 9/2000 | Favre et al. ................. 424/450 |
| 6,149,900 | A | | 11/2000 | Afriat et al. ............. 424/78.03 |
| 6,833,419 | B1 | * | 12/2004 | Morschhauser et al. .... 526/288 |
| 2003/0108497 | A1 | | 6/2003 | Chevalier |
| 2004/0024154 | A1 | | 2/2004 | Schinabeck |
| 2004/0141937 | A1 | | 7/2004 | Loeffler |

FOREIGN PATENT DOCUMENTS

WO        WO 96/37180        11/1996

* cited by examiner

*Primary Examiner*—Edward J. Webman
(74) *Attorney, Agent, or Firm*—Richard P. Silverman

(57) ABSTRACT

The invention provides acidic cosmetic, dermatological, and pharmaceutical agents comprising at least one copolymer obtainable by free-radical copolymerization of
A) acryloyldimethyltaurine and/or acryloyldimethyltaurates,
B) optionally, one or more further olefinically unsaturated, noncationic comonomers,
C) optionally, one or more olefinically unsaturated, cationic comonomers,
D) optionally, one or more silicon-containing component(s),
E) optionally, one or more fluorine-containing component(s),
F) optionally, one or more macromonomers,
G) the copolymerization taking place if desired in the presence of at least one polymeric additive,
H) with the proviso that component A) is copolymerized with at least one component selected from one of the groups D) to G).

36 Claims, No Drawings

ACID COSMETIC, DERMATOLOGICAL AND PHARMACEUTICAL AGENTS

The present invention relates to acidic cosmetic, pharmaceutical, and dermatological compositions comprising comb copolymers based on acryloyldimethyltaurine.

The cosmetic, pharmaceutical, and dermatological compositions in use at the present time mostly take the form of oil-in-water emulsions, i.e., systems composed of a continuous aqueous phase and a discontinuous, dispersed oil phase, or of water-in-oil emulsions, i.e., systems composed of a continuous, fat-containing phase and a discontinuous, dispersed aqueous phase. The water-in-oil emulsions therefore include a continuous oil phase and allow a fatty film to form at the skin surface that prevents transepidermal water loss and protects the skin against external aggressions. These emulsions are particularly suitable for protecting and enriching the skin and, in particular, for treating dry skin. The oil-in-water emulsions, for their part, impart to the skin upon application a soft, less greasy and more gentle feel than the water-in-oil emulsions.

Starting a number of years ago, the use of alpha-hydroxy acids (AHAs) in cosmetic, pharmaceutical, and dermatological compositions has become established. Particularly in the case of anti-aging products the aim is for desquamation and renewal of the topmost layers of skin of the Stratum Corneum. AHAs are used for this gentle peeling. Examples of representatives of the AHAs are glycolic acid from sugar cane, lactic acid from curdled milk, citric acid from citrus fruits, tartaric acid from wine, salicylic acid, and pyruvic acid from papaya fruits.

The use of AHAs and their salts makes it necessary in some cases to adjust the pH of the cosmetic or dermatological compositions to a distinctly acidic range.

Since the cosmetic sector uses polyelectrolytes based on (meth)acrylic acid, preferably as thickeners and gel formers, the desired low pH causes very great difficulties in ensuring that the end formulations are of adequate stability. A substantial disadvantage of the thickeners based on poly(meth) acrylic acid is the heavy pH dependence of the thickening effect. Thus, generally speaking, adequate viscosity is only developed when the pH of the formulation is adjusted to more than 6 so that the poly(meth)acrylic acid is in neutralized form.

Over the course of recent years, polymers have become established on the market which have allowed the formulation of low-surfactant emulsions and even surfactant-free pseudo emulsions (WO 96/37180 and U.S. Pat. No. 5,736, 125). By hydrophobic modification of conventional poly (meth)acrylates, an access route has been found here to polymers which may have both thickening and emulsifying/dispersing properties. Examples of commercial hydrophobically modified poly(meth)acrylates are ®Pemulen TR-1 and TR-2 from BF Goodrich and ®ACULYN 22 from Rohm & Haas. Since, however, these hydrophobically modified polymers are without exception constructed on the basis of (meth)acrylic acid, they also possess the abovementioned disadvantages of the poly(meth)acrylates and therefore in particular are not of unrestricted suitability for the formulation of acidic cosmetic, pharmaceutical, and dermatological preparations.

There is therefore a need for acidic cosmetic, dermatological, and pharmaceutical compositions which are easy to prepare and possess outstanding rheological and sensorial properties and high stability.

Surprisingly it has now been found that a new class of copolymers based on acryloyldimethyltaurine (AMPS)—and suitable in the capacity of a thickener, bodying agent, emulsifier, dispersant and/or stabilizer—are outstandingly suitable for the formulation of acidic cosmetic, pharmaceutical, and dermatological preparations.

The invention accordingly provides acidic cosmetic, dermatological, and pharmaceutical compositions comprising at least one copolymer obtainable by free-radical copolymerization of A) acryloyldimethyltaurine and/or acryloyldimethyltaurates,
B) if desired, one or more further olefinically unsaturated, noncationic, optionally crosslinking, comonomers which have at least one oxygen, nitrogen, sulfur or phosphorus atom and possess a molecular weight of less than 500 g/mol,
C) if desired, one or more olefinically unsaturated, cationic comonomers which have at least one oxygen, nitrogen, sulfur or phosphorus atom and possess a molecular weight of less than 500 g/mol,
D) if desired, one or more silicon-containing components capable of free-radical polymerization and having a functionality of at least one,
E) if desired, one or more fluorine-containing components capable of free-radical polymerization and having a functionality of at least one,
F) if desired, one or more olefinically mono- or polyunsaturated, optionally crosslinking macromonomers each possessing at least one oxygen, nitrogen, sulfur or phosphorus atom and having a number-average molecular weight of greater than or equal to 200 g/mol, the macromonomers not being a silicon-containing component D) or fluorine-containing component E),
G) the copolymerization taking place if desired in the presence of at least one polymeric additive having number-average molecular weights of from 200 g/mol to $10^9$ g/mol,
H) with the proviso that component A) is copolymerized with at least one component selected from one of the groups D) to G).

The copolymers of the invention preferably possess a molecular weight of from $10^3$ g/mol to $10^9$ g/mol, more preferably from $10^4$ to $10^7$ g/mol, with particular preference from $5*10^4$ to $5*10^6$ g/mol.

The acryloyldimethyltaurates can be the organic or inorganic salts of acryloyldimethyltaurine (acrylamidopropyl-2-methyl-2-sulfonic acid). Preference is given to the $Li^+$, $Na^+$, $K^+$, $Mg^{++}$, $Ca^{++}$, $Al^{+++}$ and/or $NH_4^+$ salts. Likewise preferred are the monoalkylammonium, dialkylammonium, trialkylammonium and/or tetraalkylammonium salts, in which the alkyl substituents of the amines may independently of one another be $(C_1-C_{22})$-alkyl radicals or $(C_2-C_{10})$-hydroxyalkyl radicals. Preference is also given to mono- to triethoxylated ammonium compounds with different degrees of ethoxylation. It should be noted that mixtures of two or more of the abovementioned representatives are also embraced by the invention.

The degree of neutralization of the acryloyldimethyltaurine can be between 0 and 100%, with particular preference being given to a degree of neutralization of more than 80%.

Based on the total mass of the copolymers, the amount of acryloyldimethyltaurine and/or acryloyldimethyltaurates is at least 0.1% by weight, preferably from 20 to 99.5% by weight, more preferably from 50 to 98% by weight.

As comonomers B) it is possible to use all olefinically unsaturated noncationic monomers whose reaction parameters allow copolymerization with acryloyldimethyltaurine and/or acryloyldimethyltaurates in the respective reaction media. Preferred comonomers B) are unsaturated carboxylic acids and their anhydrides and salts, and also their esters with aliphatic, olefinic, cycloaliphatic, arylaliphatic or aromatic alcohols having a carbon number of from 1 to 30.

Particularly preferred unsaturated carboxylic acids are acrylic acid, methacrylic acid, styrenesulfonic acid, maleic acid, fumaric acid, crotonic acid, itaconic acid, and senecic acid.

Preferred counterions are $Li^+$, $Na^+$, $K^+$, $Mg^{++}$, $Ca^{++}$, $Al^{+++}$, $NH_4^+$, monoalkylammonium, dialkylammonium, trialkylammonium and/or tetraalkylammonium radicals, in which the alkyl substituents of the amines independently of one another can be $(C_1–C_{22})$-alkyl radicals or $(C_2–C_{10})$-hydroxyalkyl radicals. It is additionally possible to employ mono- to triethoxylated ammonium compounds with a different degree of ethoxylation. The degree of neutralization of the carboxylic acids can be between 0 and 100%.

Further preferred comonomers B) are open-chain N-vinyl amides, preferably N-vinylformamide (VIFA), N-vinylmethylformamide, N-vinylmethylacetamide (VIMA) and N-vinylacetamide; cyclic N-vinyl amides (N-vinyl lactams) with a ring size of 3 to 9, preferably N-vinylpyrrolidone (NVP) and N-vinylcaprolactam; amides of acrylic and methacrylic acid, preferably acrylamide, methacrylamide, N,N-dimethyl-acrylamide, N,N-diethylacrylamide, and N,N-diisopropylacrylamide; alkoxylated acrylamides and methacrylamides, preferably hydroxyethyl methacrylate, hydroxy-methylmethacrylamide, hydroxyethylmethacrylamide, hydroxypropylmethacrylamide, and mono [2-(methacryloyloxy)ethyl] succinate; N,N-dimethylamino methacrylate; diethylaminomethyl methacrylate; acrylamido- and methacrylamido-glycolic acid; 2- and 4-vinylpyridine; vinyl acetate; glycidyl methacrylate; styrene; acrylonitrile; vinyl chloride; stearyl acrylate; lauryl methacrylate; vinylidene chloride; and/or tetrafluoroethylene.

Likewise suitable comonomers B) are inorganic acids and their salts and esters. Preferred acids are vinylphosphonic acid, vinylsulfonic acid, allylphosphonic acid, and methallylsulfonic acid.

The weight fraction of the comonomers B), based on the total mass of the copolymers, can be from 0 to 99.8% by weight and is preferably from 0.5 to 80% by weight, more preferably from 2 to 50% by weight.

Suitable comonomers C) include all olefinically unsaturated monomers with cationic charge which are capable of forming copolymers with acryloyldimethyltaurine or its salts in the chosen reaction media. The resulting distribution of the cationic charges across the chains can be random, alternating, blocklike or gradientlike. It may be noted that the cationic comonomers C) also comprehend those which bear the cationic charge in the form of a betaine, zwitterionic or amphoteric structure. Comonomers C) for the purposes of the invention are also amino-functionalized precursors which can be converted by polymer-analogous reactions into their corresponding quaternary derivatives (e.g., reaction with dimethyl sulfate, methyl chloride), zwitterionic derivatives (e.g., reaction with hydrogen peroxide), betaine derivatives (e.g., reaction with chloroacetic acid), or amphoteric derivatives.

Particularly preferred comonomers C) are
diallyldimethylammonium chloride (DADMAC),
[2-(methacryloyloxy)ethyl]trimethylammonium chloride (MAPTAC),
[2-(acryloyloxy)ethyl]trimethylammonium chloride,
[2-methacrylamidoethyl]trimethylammonium chloride,
[2-(acrylamido)ethyl]trimethylammonium chloride,
N-methyl-2-vinylpyridinium chloride,
N-methyl-4-vinylpyridinium chloride,
dimethylaminoethyl methacrylate,
dimethylaminopropylmethacrylamide,
methacryloylethyl N-oxide and/or
methacryloylethyl betaine.

The weight fraction of the comonomers C), based on the total mass of the copolymers, can be from 0.1 to 99.8% by weight, more preferably from 0.5 to 30% by weight, and very preferably from 1 to 20% by weight.

Suitable polymerizable silicon-containing components D) are all compounds which are olefinically at least monounsaturated and capable of free-radical copolymerization under the reaction conditions chosen in each case. The distribution of the individual silicone-containing monomers across the polymer chains which form need not necessarily be random. The invention also embraces the formation, for example, of blocklike (including multiblock) or gradientlike structures. Combinations of two or more different silicone-containing representatives are also possible. The use of silicone-containing components having two or more polymerization-active groups leads to the construction of branched or crosslinked structures.

Preferred silicone-containing components D) are those of formula (I).

$$R^1\text{-}Z\text{-}[(Si(R^3R^4)\text{—}O\text{—})_w\text{—}(Si(R^5R^6)\text{—}O)_x\text{—}]\text{—}R^2 \quad (I)$$

In this formula $R^1$ represents a polymerizable function from the group of the vinylically unsaturated compounds which is suitable for the synthesis of polymeric structures by a free-radical route. $R^1$ represents preferably a vinyl, ally, methallyl, methylvinyl, acryloyl ($CH_2$=$CH$—$CO$—), methacryloyl ($CH_2$=$C[CH_3]$—$CO$—), crotonyl, senecionyl, itaconyl, maleyl, fumaryl or styryl radical.

The attachment of the silicone-containing polymer chain to the reactive end group $R^1$ requires a suitable chemical bridge Z. Preferred bridges Z are —O—, $((C_1–C_{50})$alkylene), —$((C_6–C_{30})$arylene)-, —$((C_5–C_8)$cycloalkylene)-, —$((C_1–C_{50})$alkenylene)-, -(polypropylene oxide)$_n$-, -(polyethylene oxide)$_o$-, -(polypropylene-oxide)$_n$(polyethylene oxide)$_o$-, where n and o independently of one another denote numbers from 0 to 200 and the distribution of the EO/PO units can be random or in the form of blocks. Further suitable bridge groups Z are —$((C_1–C_{10})$alkyl)-$(Si(OCH_3)_2)$— and —$(Si(OCH_3)_2)$—.

The polymeric central moiety is represented by silicone-containing repeating units. The radicals $R^3$, $R^4$, $R^5$, and $R^6$ denote independently of one another —$CH_3$, —O—$CH_3$, —$C_6H_5$ or —O—$C_6H_5$.

The indices w and x represent stoichiometric coefficients which amount independently of one another to from 0 to 500, preferably 10 to 250.

The distribution of the repeating units across the chain can be not only purely random but also blocklike, alternating or gradientlike.

$R^2$ stands for an aliphatic, olefinic, cycloaliphatic, arylaliphatic or aromatic $(C_1–C_{50})$ hydrocarbon radical (linear or branched) or —OH, —$NH_2$, —$N(CH_3)_2$, —$R^7$ or for the structural unit [-Z-$R^1$]. The definition of the two variables Z and $R^1$ has already been explained. $R^7$ stands for further Si-containing groups. Preferred radicals $R^7$ are —O—Si$(CH_3)_3$, —O—Si$(Ph)_3$, —O—Si(O—Si$(CH_3)_3)_2CH_3$) and —O—Si(O—Si$(Ph)_3)_2$Ph. If $R^2$ is an element of the group [-Z-$R^1$] the monomers in question are difunctional monomers which can be used to crosslink the polymer structures which form. Formula (I) describes not only silicone-containing polymer species with vinylic functionalization and a polymer-typical distribution, but also defined compounds having discrete molecular weights.

Particularly preferred silicone-containing components are the following components with acrylic or methacrylic modification:

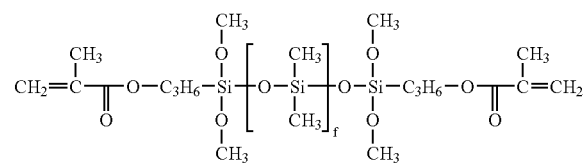

methacryloyloxypropylmethylsilyl-endblocked polydimethylsiloxanes (f=2 to 500)

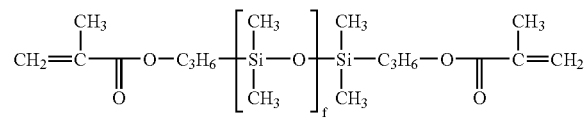

methacryloyloxypropyl-endblocked polydimethylsiloxanes (f=2 to 500)

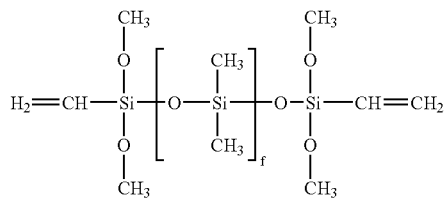

vinyldimethoxysilyl-endblocked polydimethylsiloxanes (f=2–500).

Based on the total mass of the copolymers, suitable silicon-containing components can be present in an amount of up to 99.9% by weight, preferably from 0.5 to 30% by weight, more preferably from 1 to 20% by weight.

Suitable polymerizable fluorine-containing components E) include all compounds which are olefinically at least monounsaturated and which are capable of free-radical copolymerization under the reaction conditions chosen in each case. The distribution of the individual fluorine-containing monomers across the polymer chains which form need not necessarily be random. The invention also embraces the formation of blocklike (including multiblock) or gradientlike structures, for example. Combinations of two or more different fluorine-containing components E) are also possible, it being clear to the expert that monofunctional representatives lead to the formation of comb-shaped structures while di-, tri-, or polyfunctional components E) lead to structures which are at least partly crosslinked.

Preferred fluorine-containing components E) are those of formula (II).

In this formula $R^1$ represents a polymerizable function from the group of the vinylically unsaturated compounds which is suitable for the construction of polymeric structures by a free-radical route. $R^1$ is preferably a vinyl, allyl, methallyl, methylvinyl, acryloyl ($CH_2$=CH—CO—), methacryloyl ($CH_2$=C[$CH_3$]—CO—), crotonyl, senecionyl, itaconyl, maleyl, fumaryl or styryl radical, more preferably an acryloyl or methacryloyl radical.

The attachment of the fluorine-containing group to the reactive end group $R^1$ requires a suitable chemical bridge Y. Preferred bridges Y are —O—, —C(O)—, —C(O)—O—, —S—, —O—$CH_2$—CH(O—)—$CH_2$OH, —O—$CH_2$—CH(OH)—$CH_2$—O—, —O—$SO_2$—O—, —O—S(O)—O—, —PH—, —P($CH_3$)—, —$PO_3$—, —NH—, —N($CH_3$)—, —O—($C_1$–$C_{50}$)alkyl-O—, —O-phenyl-O—, —O-benzyl-O—, —O—($C_5$–$C_8$)cycloalkyl-O—, —O—($C_1$–$C_{50}$)alkenyl-O—, —O—(CH($CH_3$)—$CH_2$—O)$_n$—, —O—($CH_2$—$CH_2$—O)$_n$—, and —O—([CH—$CH_2$—O]$_n$—[$CH_2$—$CH_2$—O]$_m$)$_o$—, where n, m, and o independently of one another denote numbers from 0 to 200 and the distribution of the EO and PO units can be random or in the form of blocks. r and s are stoichiometric coefficients which independently of one another denote numbers from 0 to 200.

Preferred fluorine-containing components E) of formula (II) are
perfluorohexylethanol methacrylate,
perfluorohexoylpropanol methacrylate,
perfluoroctylethanol methacrylate,
perfluoroctylpropanol methacrylate,
perfluorohexylethanolyl polyglycol ether methacrylate,
perfluorohexoylpropanolyl poly[ethylglycol-co-propylene glycol ether] acrylate,
perfluoroctylethanolyl poly[ethylglycol-block-co-propylene glycol ether] methacrylate,
perfluoroctylpropanolyl polypropylene glycol ether methacrylate.

Based on the total mass of the copolymers the amount of suitable fluorine-containing components can be up to 99.9% by weight, preferably from 0.5 to 30% by weight, more preferably from 1 to 20% by weight.

The macromonomers F) are at least singly olefinically functionalized polymers having one or more discrete repeating units and a number-average molecular weight of greater than or equal to 200 g/mol. In the copolymerization it is also possible to use mixtures of chemically different macromonomers F). The macromonomers are polymeric structures composed of one or more repeating units and have a molecular weight distribution characteristic of polymers. Preferred macromonomers F) are compounds of formula (III).

$R^1$ represents a polymerizable function from the group of the vinylically unsaturated compounds which are suitable for constructing polymeric structures by a free-radical route. Preferably $R^1$ is a vinyl, allyl, methallyl, methylvinyl, acryloyl ($CH_2$=CH—CO—), methacryloyl ($CH_2$=([$CH_3$]—CO—), crotonyl, senecionyl, itaconyl, maleyl, fumaryl or styryl radical.

Attachment of the polymer chain to the reactive end group requires a suitable bridging group Y. Preferred bridges Y are —O—, —C(O)—, —C(O)—O—, —S—, —O—$CH_2$—CH(O—)—$CH_2$OH, —O—$CH_2$—CH(OH)—$CH_2$O—, —O—$SO_2$—O—, —O—$SO_2$—O—, —O—SO—O—, —PH—, —P($CH_3$)—, —$PO_3$—, —NH—, and —N($CH_3$)—, more preferably —O—.

The polymeric central moiety of the macromonomer is represented by the discrete repeating units A, B, C, and D. Preferably the repeating units A, B, C, and D are derived from: acrylamide, methacrylamide, ethylene oxide, propylene oxide, AMPS, acrylic acid, methacrylic acid, methyl methacrylate, acrylonitrile, maleic acid, vinyl acetate, styrene, 1,3-butadiene, isoprene, isobutene, diethylacrylamide, and diisopropylacrylamide.

The indices v, w, x, and z in formula (III) represent the stoichiometric coefficients relating to the repeating units A, B, C, and D. v, w, x, and z amount independently of one another to from 0 to 500, preferably 1 to 30, it being necessary for the sum of the four coefficients on average to be $\geq 1$.

The distribution of the repeating units over the macromonomer chain can be random, blocklike, alternating or gradientlike.

$R^2$ denotes a linear or branched aliphatic, olefinic, cycloaliphatic, arylaliphatic or aromatic $C_1$–$C_{50}$ hydrocarbon radical, OH, —$NH_2$, —$N(CH_3)_2$ or is the structural unit [—Y—$R^1$].

In the case of $R^2$ being [—Y—$R^1$] the macromonomers in question are difunctional and suitable for crosslinking the copolymers.

Particularly preferred macromonomers F) are acrylically or methacrylically monofunctionalized alkyl ethoxylates of formula (IV).

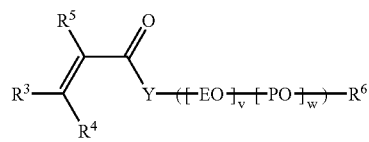

(IV)

$R_3$, $R_4$, $R_5$, and $R_6$ are independently of one another hydrogen or n-aliphatic, iso-aliphatic, olefinic, cycloaliphatic, arylaliphatic or aromatic $C_1$–$C_{30}$ hydrocarbon radicals.

Preferably $R_3$ and $R_4$ are H or —$CH_3$, more preferably H; $R_5$ is H or —$CH_3$; and $R_6$ is an n-aliphatic, iso-aliphatic, olefinic, cycloaliphatic, arylaliphatic or aromatic $C_1$–$C_{30}$ hydrocarbon radical.

v and w are in turn the stoichiometric coefficients relating to the ethylene oxide units (EO) and propylene oxide units (PO). v and w amount independently of one another to from 0 to 500, preferably 1 to 30, it being necessary for the sum of v and w to be on average $\geq 1$. The distribution of the EO and PO units over the macromonomer chain can be random, blocklike, alternating or gradientlike. Y stands for the above-mentioned bridges.

Further particularly preferred macromonomers F) have the following structure in accordance with formula (IV):

| Name | $R^3$ | $R^4$ | $R^5$ | $R^6$ | v | w |
|---|---|---|---|---|---|---|
| ®LA-030-methacrylate | H | H | —$CH_3$ | -lauryl | 3 | 0 |
| ®LA-070-methacrylate | H | H | —$CH_3$ | -lauryl | 7 | 0 |
| ®LA-200-methacrylate | H | H | —$CH_3$ | -lauryl | 20 | 0 |
| ®LA-250-methacrylate | H | H | —$CH_3$ | -lauryl | 25 | 0 |
| ®T-080-methacrylate | H | H | —$CH_3$ | -talc | 8 | 0 |
| ®T-080-acrylate | H | H | H | -talc | 8 | 0 |
| ®T-250-methacrylate | H | H | —$CH_3$ | -talc | 25 | 0 |
| ®T-250-crotonate | —$CH_3$ | H | —$CH_3$ | -talc | 25 | 0 |
| ®OC-030-methacrylate | H | H | —$CH_3$ | -octyl | 3 | 0 |
| ®OC-105-methacrylate | H | H | —$CH_3$ | -octyl | 10 | 5 |
| ®Behenyl-010-methylaryl | H | H | H | -behenyl | 10 | 0 |
| ®Behenyl-020-methylaryl | H | H | H | -behenyl | 20 | 0 |
| ®Behenyl-010-senecionyl | —$CH_3$ | —$CH_3$ | H | -behenyl | 10 | 0 |
| ®PEG-440-diacrylate | H | H | H | -acryloyl | 10 | 0 |
| ®B-11-50-methacrylate | H | H | —$CH_3$ | -butyl | 17 | 13 |
| ®MPEG-750-methacrylate | H | H | —$CH_3$ | -methyl | 18 | 0 |
| ®P-010-acrylate | H | H | H | -phenyl | 10 | 0 |
| ®O-050-acrylate | H | H | H | -oleyl | 5 | 0 |

Further particularly suitable macromonomers F) are esters of (meth)acrylic acid with
($C_{10}$–$C_{18}$) fatty alcohol polyglycol ethers having 8 EO units (Genapol® C-080)
$C_{11}$ oxo alcohol polyglycol ethers having 8 EO units (Genapol® UD-080)
($C_{12}$–$C_{14}$) fatty alcohol polyglycol ethers having 7 EO units (Genapol® LA-070)
($C_{12}$–$C_{14}$) fatty alcohol polyglycol ethers having 11 EO units (Genapol® LA-110)
($C_{16}$–$C_{18}$) fatty alcohol polyglycol ethers having 8 EO units (Genapol® T-080)
($C_{16}$–$C_{18}$) fatty alcohol polyglycol ethers having 15 EO units (Genapol® T-150)
($C_{16}$–$C_{18}$) fatty alcohol polyglycol ethers having 11 EO units (Genapol® T-110)
($C_{16}$–$C_{18}$) fatty alcohol polyglycol ethers having 20 EO units (Genapol® T-200)
($C_{16}$–$C_{18}$) fatty alcohol polyglycol ethers having 25 EO units (Genapol® T-250)
($C_{18}$–$C_{22}$) fatty alcohol polyglycol ethers having 25 EO units and/or
iso-($C_{16}$–$C_{18}$) fatty alcohol polyglycol ethers having 25 EO units.

The Genapol® grades are products of Clariant GmbH.

The molecular weight of the macromonomers F) is preferably from 200 g/mol to $10^6$ g/mol, more preferably from 150 to $10^4$ g/mol, and very preferably from 200 to 5 000 g/mol.

Based on the total mass of the copolymers it is possible for the amount of macromonomers to be up to 99.9% by weight, preferably from 0.5 to 30% by weight or from 70 to 99.5% by weight. Particularly preferred are amounts of from 1 to 20% by weight or from 75 to 95% by weight.

Preferred copolymers are those obtainable by copolymerizing at least components A) and F).

Further preferred copolymers are those obtainable by copolymerizing at least components A) and D).

Further preferred copolymers are those obtainable by copolymerizing at least components A) and E).

Further preferred copolymers are those obtainable by copolymerizing at least components A), C) and D).

Further preferred copolymers are those obtainable by coppolymerizing at least components A), C) and E).

Further preferred copolymers are those obtainable by copolymerizing at least components A), D) and F).

In one preferred embodiment the copolymerization is conducted in the presence of at least one polymeric additive G), the additive G) being added wholly or partly in solution to the polymerization medium before the actual copolymerization. The use of two or more additives G) is likewise in accordance with the invention. Crosslinked additives G) may likewise be used.

The additives G) or mixtures thereof must only be wholly or partly soluble in the chosen polymerization medium. During the actual polymerization step the additive G) has a number of functions. On the one hand it prevents the formation of overcrosslinked polymer fractions in the copolymer which forms in the actual polymerization step, and on the other hand the additive G) is statistically attacked by active free radicals in accordance with the very well-known mechanism of graft copolymerization. Depending on the particular additive G), this results in greater or lesser fractions of the additive being incorporated into the copolymers. Moreover, suitable additives G) possess the property of altering the solution parameters of the copolymers which form during the free-radical polymerization reaction in such a way that the average molecular weights are shifted to higher values. As compared with analogous copolymers prepared without the addition of the additives G), those prepared with the addition of additives G) advantageously exhibit a significantly higher viscosity in aqueous solution.

Preferred additives G) are homopolymers and copolymers which are soluble in water and/or alcohols, preferably in t-butanol. The term "copolymers" also comprehends those having more than two different monomer types. Particularly preferred additives G) are homopolymers and copolymers of N-vinylformamide, N-vinylacetamide, N-vinylpyrrolidone, ethylene oxide, propylene oxide, acryloyldimethyltaurine, N-vinylcaprolactam, N-vinylmethylacetamide, acrylamide, acrylic acid, methacrylic acid, N-vinylmorpholide, hydroxyethyl methacrylate, diallyldimethylammonium chloride (DADMAC) and/or [2-(methacryloyloxy)ethyl]trimethylammonium chloride (MAPTAC); polyalkylene glycols and/or alkylpolyglycols.

Particularly preferred additives G) are polyvinylpyrrolidones (e.g., Luviskol K15®, K20® and K30® from BASF), poly(N-vinylformamides), poly(N-vinylcaprolactams), and copolymers of N-vinylpyrrolidone, N-vinylformamide and/or acrylic acid, which may also have been partly or fully hydrolyzed.

The molecular weight of the additives G) is preferably from $10^2$ to $10^7$ g/mol, more preferably from $0.5*10^4$ to $10^6$ g/mol.

The amount in which the polymeric additive G) is used, based on the total mass of the monomers to be polymerized during the copolymerization, is preferably from 0.1 to 90% by weight, more preferably from 1 to 20% by weight, and with particular preference from 1.5 to 10% by weight.

In another preferred embodiment the copolymers of the invention are crosslinked, i.e., they contain comonomers having at least two polymerizable vinyl groups. Preferred crosslinkers are methylenebisacrylamide; methylenebismethacrylamide; esters of unsaturated monocarboxylic and polycarboxylic acids with polyols, preferably diacrylates and triacrylates, dimethacrylates and trimethacrylates, more preferably butanediol and ethylene glycol diacrylate and methacrylate, trimethylolpropane triacrylate (TMPTA) and trimethylolpropane trimethacrylate (TMPTMA); allyl compounds, preferably allyl (meth)acrylate, triallyl cyanurate, diallyl maleate, polyallyl esters, tetraallyloxyethane, triallylamine, tetraallylethylenediamine; allyl esters of phosphoric acid; and/or vinylphosphonic acid derivatives. A particularly preferred crosslinker is trimethylolpropane triacrylate (TMPTA). The weight fraction of crosslinking comonomers, based on the total mass of the copolymers, is preferably up to 20% by weight, more preferably from 0.05 to 10% by weight, and very preferably from 0.1 to 7% by weight.

The polymerization medium used may comprise all organic or inorganic solvents which have a very substantially inert behavior with respect to free-radical polymerization reactions and which advantageously allow the formation of medium or high molecular weights. Those used preferably include water; lower alcohols; preferably methanol, ethanol, propanols, iso-, sec- and t-butanol, very preferably t-butanol; hydrocarbons having 1 to 30 carbon atoms, and mixtures of the aforementioned compounds.

The polymerization reaction takes place preferably in the temperature range between 0 and 150° C., more preferably between 10 and 100° C., either at atmospheric pressure or under elevated or reduced pressure. If desired the polymerization may also be performed under an inert gas atmosphere, preferably under nitrogen.

In order to initiate the polymerization it is possible to use high-energy electro-magnetic rays, mechanical energy, or the customary chemical polymerization initiators, such as organic peroxides, e.g., benzoyl peroxide, tert-butyl hydroperoxide, methyl ethyl ketone peroxide, cumene hydroperoxide, dilauroyl peroxide or azo initiators, such as azodiisobutyronitrile (AIBN), for example. Likewise suitable are inorganic peroxy compounds, such as $(NH_4)_2S_2O_8$, $K_2S_2O_8$ or $H_2O_2$, for example, where appropriate in combination with reducing agents (e.g., sodium hydrogensulfite, ascorbic acid, iron(II) sulfate, etc.) or redox systems comprising as reducing component an aliphatic or aromatic sulfonic acid (e.g., benzenesulfonic acid, toluenesulfonic acid, etc.).

Serving as the polymerization medium may be any solvents which are very substantially inert in respect of free-radical polymerization reactions and which allow the development of high molecular weights. Use is preferably made of water and lower, tertiary alcohols or hydrocarbons having 3 to 30 carbon atoms. In one particularly preferred embodiment t-butanol is used as the reaction medium. Mixtures of two or more representatives of the potential solvents described are of course likewise in accordance with the invention. This also includes emulsions of mutually immiscible solvents (e.g., water/hydrocarbons). In principle, all kinds of reaction regime leading to the polymer structures of the invention are suitable (solution polymerization, emulsion methods, precipitation methods, high-pressure methods, suspension methods, bulk polymerization, gel polymerization, and so on). Preferred suitability is possessed by precipitation polymerization, particularly preferred suitability by precipitation polymerization in tert-butanol.

The following list shows 67 copolymers suitable with particular advantage for formulating the compositions of the invention. The different copolymers 1 to 67 are obtainable in accordance with the following preparation processes 1, 2, 3, and 4.

Process 1:

These polymers can be prepared by the precipitation method in tert-butanol. The monomers were introduced in t-butanol, the reaction mixture was rendered inert, and then, after initial heating to 60° C., the reaction was initiated by addition of the corresponding t-butanol-soluble initiator (preferably dilauroyl peroxide). After the end of reaction (2 hours) the polymers were isolated by removal of the solvent under suction and by subsequent vacuum drying.

Process 2:

These polymers are preparable by the gel polymerization method in water. The monomers are dissolved in water, the reaction mixture is rendered inert, and then, after initial heating to 65° C., the reaction is initiated by addition of suitable initiators or initiator systems (preferably $Na_2S_2O_8$). The polymer gels are subsequently comminuted and the polymers are isolated after drying.

Process 3:

These polymers are preparable by the emulsion method in water. The monomers are emulsified in a mixture of water/organ. solvent (preferably cyclohexane) using an emulsifier, the reaction mixture is rendered inert by means of $N_2$, and then, after initial heating to 80° C., the reaction is initiated by addition of suitable initiators or initiator systems (preferably $Na_2S_2O_8$). The polymer emulsions are subsequently evaporated down (with cyclohexane acting as an azeotrope former for water) and the polymers are thereby isolated.

Process 4:

These polymers are preparable by the solution method in organic solvents (preferably-toluene, also, for example, tertiary alcohols). The monomers are introduced in the solvent, the reaction mixture is rendered inert, and then, after initial heating to 70° C., the reaction is initiated by addition of suitable initiators or initiator systems (preferably dilauroyl peroxide). The polymers are isolated by evaporating off the solvent and by subsequent vacuum drying.

Polymers having hydrophobic side chains, uncrosslinked

| No. | Composition | Preparation process |
|---|---|---|
| 1 | 95 g AMPS 5 g Genapol T-080 | 1 |
| 2 | 90 g AMPS 10 g Genapol T-080 | 1 |
| 3 | 85 g AMPS 15 g Genapol T-080 | 1 |
| 4 | 80 g AMPS 20 g Genapol T-080 | 1 |
| 5 | 70 g AMPS 30 g Genapol T-080 | 1 |
| 6 | 50 g AMPS 50 g Genapol T-080 | 3 |
| 7 | 40 g AMPS 60 g Genapol T-080 | 3 |
| 8 | 30 g AMPS 70 g Genapol T-080 | 3 |
| 9 | 20 g AMPS 80 g Genapol T-080 | 3 |
| 10 | 60 g AMPS 60 g BB10 | 4 |
| 11 | 80 g AMPS 20 g BB10 | 4 |
| 12 | 90 g AMPS 10 g BB10 | 3 |
| 13 | 80 g AMPS 20 g BB10 | 1 |
| 14 | 80 g AMPS 20 g Genapol LA040 | 1 |

Polymers having hydrophobic side chains, crosslinked

| No. | Composition | Preparation process |
|---|---|---|
| 15 | 80 g AMPS 20 g Genapol LA040 0.6 g AMA | 1 |
| 16 | 80 g AMPS 20 g Genapol LA040 0.8 g AMA | 1 |
| 17 | 80 g AMPS 20 g Genapol LA040 1.0 g AMA | 1 |
| 18 | 628.73 g AMPS 120.45 g Genapol T-250 6.5 g TMPTA | 2 |
| 19 | 60 g AMPS 40 g BB10 1.9 g TMPTA | 4 |
| 20 | 80 g AMPS 20 g BB10 1.4 g TMPTA | 4 |
| 21 | 90 g AMPS 10 g BB10 1.9 g TMPTA | 4 |
| 22 | 80 g AMPS 20 g BB10 1.9 g TMPTA | 4 |
| 23 | 60 g AMPS 40 g BB10 1.4 g TMPTA | 4 |

Polymers having hydrophobic side chains, crosslinked, grafted

| No. | Composition | Preparation process |
|---|---|---|
| 24 | 95 g AMPS 5 g BB10, 1.9 g TMPTA, 1 g Poly-NVP | 1 |
| 25 | 90 g AMPS 10 g BB10, 1.9 g TMPTA, 1 g Poly-NVP | 1 |
| 26 | 85 g AMPS 15 g BB10, 1.9 g TMPTA, 1 g Poly-NVP | 1 |
| 27 | 90 g AMPS 10 g BB10, 1.9 g TMPTA, 1 g Poly-NVP | 1 |

Polymers having silicon-containing groups, uncrosslinked

| No. | Composition | Preparation process |
|---|---|---|
| 28 | 80 g AMPS, 20 g Silvet 867 | 1 |
| 29 | 80 g AMPS, 50 g Silvet 867 | 4 |

Polymers having silicon-containing groups, crosslinked

| No. | Composition | Preparation process |
|---|---|---|
| 30 | 80 g AMPS, 20 g Silvet 867, 0.5 g MBA | 4 |
| 31 | 80 g AMPS, 20 g Silvet 867, 1.0 g MBA | 1 |
| 32 | 60 g AMPS, 40 g Y-12867, 0.95 g AMA | 1 |
| 33 | 80 g AMPS, 20 g Y-12867, 0.95 g AMA | 1 |
| 34 | 90 g AMPS, 10 g Y-12867, 0.95 g AMA | 1 |
| 35 | 60 g AMPS, 40 g Silvet 7280, 0.95 g AMA | 1 |
| 36 | 80 g AMPS, 20 g Silvet 7280, 0.95 g AMA | 1 |
| 37 | 90 g AMPS, 10 g Silvet 7280, 0.95 g AMA | 1 |
| 38 | 60 g AMPS, 40 g Silvet 7608, 0.95 g AMA | 1 |
| 39 | 80 g AMPS, 20 g Silvet 7608, 0.95 g AMA | 1 |
| 40 | 90 g AMPS, 10 g Silvet 7608, 0.95 g AMA | 1 |

Polymers having hydrophobic side chains and cationic groups, uncrosslinked

| No. | Composition | Preparation process |
|---|---|---|
| 41 | 87.5 g AMPS, 7.5 g Genapol T-110, 5 g DADMAC | 2 |
| 42 | 40 g AMPS, 10 g Genapol T110, 45 g methacrylamide | 2 |
| 43 | 55 g AMPS, 40 g Genapol LA040, 5 g Quat | 1 |
| 44 | 75 g AMPS, 10 g BB10, 6.7 g Quat | 1 |

Polymers having hydrophobic side chains and cationic groups, crosslinked

| No. | Composition | Preparation process |
|---|---|---|
| 45 | 60 g AMPS, 20 g Genapol T-80, 10 g Quat, 10 g HEMA | 1 |
| 46 | 75 g AMPS, 20 g Genapol T-250, 5 g Quat, 1.4 g TMPTA | 1 |

-continued

| No. | Composition | Preparation process |
|---|---|---|
| 47 | 75 g AMPS, 20 g Genapol T-250, 10 g Quat, 1.4 g TMPTA | 1 |
| 48 | 75 g AMPS, 20 g Genapol T-250, 20 g Quat, 1.4 g TMPTA | 1 |

Polymers having fluorine-containing groups

| No. | Composition | Preparation process |
|---|---|---|
| 49 | 94 g AMPS, 2.02 g Fluowet AC 600 | 1 |
| 50 | 80 g AMPS, 20 g perfluorooctylpolyethylene glycol methacrylate, 1 g Span 80 | 3 |

Polymers having fluorine-containing groups, grafted

| No. | Composition | Preparation process |
|---|---|---|
| 51 | 80 g AMPS, 10 g Fluowet AC 600, 5 g Poly-NVP | 1 |
| 52 | 70 g AMPS, 8 g perfluorooctylethyloxyglyceryl methacrylate, 5 g Poly-NVP | 4 |

Polyfunctional polymers

| No. | Composition | Preparation process |
|---|---|---|
| 53 | 80 g AMPS, 10 g Genapol LA070, 10 g Silvet 7608, 1.8 g TMPTA | 1 |
| 54 | 70 g AMPS, 5 g N-vinylpyrrolidone, 15 g Genapol T-250 methacrylate, 10 g Quat, 10 g Poly-NVP | 4 |
| 55 | 80 g AMPS, 5 g N-vinylformamide, 5 g Genapol O-150-methacrylate, 10 g DADMAC, 1.8 g TMPTA, 8 g poly-N-vinylformamide | 2 |
| 56 | 70 g AMPS, 5 g N-vinylpyrrolidone, 15 g Genapol T-250-methacrylate, 10 g Quat, 10 g Poly-NVP | 1 |
| 57 | 60 g AMPS, 10 g Genapol-BE-020-methacrylate, 10 g Genapol T-250-acrylate, 20 g Quat, 1 g Span 80 | 1 |
| 58 | 60 g AMPS, 20 g MPEG-750-methacrylate, 10 g methacryloyloxypropyldimethicone, 10 g perfluorooctylpolyethylene glycol methacrylate, 10 g poly[N-vinylcaprolactone-co-acrylic acid] (10/90) | 1 |
| 59 | 80 g AMPS, 5 g N-vinylformamide, 5 g Genapol O-150-methacrylate, 10 g DADMAC, 1.8 g TMPTA | 1 |
| 60 | 70 g AMPS, 10 g Genapol T-250-acrylate, 5 g N-methyl-4-vinylpyridinium chloride, 2.5 g Silvet Y-12867, 2.5 g perfluorohexylpolyethylene glycol methacrylate, 10 g polyethylene glycol dimethacrylate, 4 g poly[N-vinylcaprolactam] | 1 |
| 61 | 10 g AMPS, 20 g acrylamide, 30 g N-2-vinylpyrrolidone, 20 g Silvet 7608, 10 g methacryloyloxypropyldimethicone, 10 g Fluowet AC 812 | 3 |
| 62 | 60 g AMPS, 10 g DADMAC, 10 g Quat, 10 g Genapol-LA-250-crotonate, 10 g methacryloyloxypropyldimethicone, 7 g poly[acrylic acid-co-N-vinylformamide] | 1 |
| 63 | 50 g AMPS, 45 g Silvet 7608, 1.8 g TMPTA, 8 g poly[N-vinylformamide] | 1 |
| 64 | 20 g AMPS, 10 g Genapol T 110, 35 g MAA, 30 g HEMA, 5 g DADMAC | 4 |
| 65 | 20 g AMPS, 80 g BB10, 1.4 g TMPTA | 1 |
| 66 | 75 g AMPS, 20 g BB10, 6.7 g Quat, 1.4 g TMPTA | 1 |
| 67 | 35 g AMPS, 60 g acrylamide, 2 g VIFA, 2.5 g vinylphosphonic acid, 2 mol % Fluowet EA-600 | 4 |

Chemical designation of the reactants:

| | |
|---|---|
| AMPS | acryloyldimethyltaurate, either Na or NH4 salt |
| Genapol ® T-080 | $C_{16}$–$C_{18}$ fatty alcohol polyglycol ether having 8 EO units |
| Genapol ® T-110 | $C_{12}$–$C_{14}$ fatty alcohol polyglycol ether having 11 EO units |
| Genapol ® T-250 | $C_{16}$–$C_{18}$ fatty alcohol polyglycol ether having 25 EO units |
| Genapol ® LA-040 | $C_{12}$–$C_{14}$ fatty alcohol polyglycol ether having 4 EO units |
| Genapol ® LA-070 | $C_{12}$–$C_{14}$ fatty alcohol polyglycol ether having 7 EO units |
| Genapol ® O-150 methacrylate | $C_{16}$–$C_{18}$ fatty alcohol polyglycol ether methacrylate having 15 EO units, |
| Genapol ® LA-250 crotonate | $C_{12}$–$C_{14}$ fatty alcohol polyglycol ether crotonate having 25 EO units |
| Genapol ® T-250 methacrylate | $C_{16}$–$C_{18}$ fatty alcohol polyglycol ether methacrylate having 25 EO units |
| Genapol ® T-250 acrylate | $C_{16}$–$C_{18}$ fatty alcohol polyglycol ether acrylate having 25 EO units |
| BB10 ® | polyoxyethylene(10)behenyl ether |
| TMPTA | trimethylolpropanetriacrylate |
| Poly-NVP | poly-N-vinylpyrrolidone |
| Silvet ® 867 | siloxane-polyalkylene oxide copolymer |
| MBA | methylenebisacrylamide |
| AMA | allyl methacrylate |
| ®Y-12867 | siloxane-polyalkylene oxide copolymer |
| Silvet ® 7608 | polyalkylene oxide-modified heptamethyltrisiloxane |
| Silvet ® 7280 | polyalkylene oxide-modified heptamethyltrisiloxane |
| DADMAC | diallyldimethylammonium chloride |
| HEMA | 2-hydroxyethyl methacrylate |
| Quat | 2-(methacryloyloxy)ethyltrimethylammonium chloride |
| Fluowet ® AC 600 | perfluoroalkylethyl acrylate |
| Span ® 80 | sorbitan ester |

In one preferred embodiment the copolymers are water-soluble or water-swellable.

The compositions of the invention comprise, based on the finished compositions, preferably from 0.01 to 10% by weight, more preferably from 0.1 to 5% by weight, with particular preference from 0.5 to 3% by weight, of copolymers.

The described grafting of the copolymers with other polymers, which can be carried out optionally, leads to products having a particular polymer morphology and giving rise to optically clear gels in aqueous systems. A potential disadvantage of the copolymers without grafting is a more or less strong opalescence in aqueous solution. The basis for this opalescence is hitherto unavoidable, over-crosslinked polymer fractions which arise in the course of the synthesis and are inadequately swollen in water. This produces light-scattering particles whose size is well above the wavelength of visible light and which are therefore the cause of the opalescence. The described grafting process, which can be carried out optionally, substantially reduces or entirely prevents the formation of overcrosslinked polymer fractions in relation to conventional techniques.

The described incorporation both of cationic charges and of silicon, fluorine or phosphorus atoms into the copolymers, which can be carried out optionally, leads to products which in cosmetic formulations possess particular sensorial and rheological properties. An improvement in the sensorial and rheological properties may be desired in particular in the context of use in rinse-off products (especially hair treatment compositions) or leave-on products (especially O/W emulsions). In both crosslinked and uncrosslinked form the copolymers exhibit advantageous properties. While crosslinked systems, for example, have exhibited outstanding profiles of properties in respect of emulsion stabilization, it has been possible in particular with the aid of the uncrosslinked versions to thicken surfactant-containing solutions. The same is true of electrolyte-containing systems, which are known to be very difficult if not impossible to thicken with polyelectrolytes.

The copolymers can be used as thickeners for compositions on an aqueous or aqueous-alcoholic basis, examples being hair gels. The polymers of the invention are additionally suitable as stabilizers, dispersants, and bodying agents for aqueous surfactant preparations, examples being shampoos, shower baths, shower gels, foam baths, and the like. The thickening action of the copolymers in aqueous surfactant compositions is boosted by an association between the polymer side chains and the surfactants, and can be controlled through the choice of the side chains of the copolymers and through the choice of the surfactants. The suspending or dispersing and stabilizing action of the copolymers in aqueous surfactant compositions is due to the association of the polymer side chains and/or functional groups in main chain and side chain with the liquid components that are insoluble in aqueous surfactant compositions, examples being silicone oils, and/or the insoluble components, an example being zinc pyrithione.

The copolymers are likewise suitable as thickeners and dispersants, as emulsifiers, suspension media with thickening effect, and bodying agents for emulsions and suspensions, and also as lubricants, tackifiers, thickeners, dispersants and emulsifiers of decorative preparations containing solids. In this context it is also possible to use mixtures of the copolymers. The emulsifying, stabilizing and/or bodying action of the copolymers in emulsions is due to and/or boosted by an association of the polymer side chains with one another, and also by an interaction of the polymer side chains with the hydrophobic oil components.

The pH of the cosmetic, pharmaceutical, and dermatological compositions is preferably less than or equal to 6.5, more preferably in the range from 2 to 6.5, very preferably in the range from 3 to 6.

As acidic components the compositions comprise organic or inorganic acids, preferably organic acids, very preferably alpha-hydroxy acids and acids selected from glycolic acid, lactic acid, citric acid, tartaric acid, mandelic acid, salicylic acid, ascorbic acid, pyruvic acid, oligooxa-monocarboxylic and -dicarboxylic acids, fumaric acid, retinoic acid, aliphatic and organic sulfonic acids, benzoic acid, kojic acid, fruit acid, malic acid, gluconic acid, galacturonic acid, acidic plant extracts and/or fruit extracts, and derivatives thereof.

The fraction of the acids in compositions is preferably from 0.05 to 20% by weight, more preferably from 0.5 to 10% by weight, very preferably from 1 to 5% by weight.

In one preferred embodiment compositions are emulsions, preferably oil-in-water emulsions, preferably having viscosities of from 8 000 mPas to 50 000 mPas (RV Brookfield viscometer, 20 rpm) and a pH of from 3 to 6.

In another preferred embodiment the compositions are aqueous gels, preferably aqueous gels comprising organic solvents, preferably having viscosities of from 15 000 mPas to 100 000 mPas (RV Brookfield viscometer, 20 rpm) and a pH of from 3 to 6.

In a further preferred embodiment compositions are surfactant-containing formulations, more preferably shampoos, shower baths, and the like, preferably having viscosities of from 1 000 mPas to 15 000 mPas (RV Brookfield viscometer, 20 rpm) and a pH of from 3 to 6.

The acidic components in the compositions can be present either in acid form or in the form of their salts, preferably in the form of the sodium, potassium or ammonium salts.

The compositions of the invention may comprise anionic, cationic, nonionic, zwitterionic and/or amphoteric surfactants.

The total amount of the surfactants used, based on the finished compositions, is preferably between 2 to 70% by weight, more preferably between 5 and 40% by weight, very preferably between 12 and 35% by weight.

Suitable anionic surfactants include preferably $(C_{10}-C_{20})$-alkyl and alkylene carboxylates, alkyl ether carboxylates, fatty alcohol sulfates, fatty alcohol ether sulfates, alkylamide sulfates and sulfonates, fatty acid alkylamide polyglycol ether sulfates, alkanesulfonates and hydroxyalkanesulfonates, olefinsulfonates, acyl esters of isethionates, α-sulfo fatty acid esters, alkylbenzenesulfonates, alkylphenol glycol ethersulfonates, sulfosuccinates, sulfosuccinic monoesters and diesters, fatty alcohol ether phosphates, protein/fatty acid condensation products, alkyl monoglyceride sulfates and sulfonates, alkylglyceride ether sulfonates, fatty acid methyltaurides, fatty acid sarcosinates, sulforicinoleates, and acylglutamates. The compounds and their mixtures are used in the form of their water-soluble or water-dispersible salts, examples being the sodium, potassium, magnesium, ammonium, mono-, di-, and triethanolammonium, and analogous alkylammonium salts.

The weight fraction of the anionic surfactants, based on the finished compositions, is preferably in the range from 2 to 30% by weight, more preferably from 5 to 25% by weight, very preferably from 12 to 22% by weight.

Suitable cationic surfactants include for example quaternary ammonium salts such as di-$(C_{10}-C_{24})$-alkyl-dimethylammonium chloride or bromide, preferably di-$(C_{12}-C18)$-alkyl-dimethylammonium chloride or bromide; $(C_{10}-C_{24})$-alkyl-dimethylethylammonium chloride or bromide; $(C_{10}-C_{24})$-alkyl-trimethylammonium chloride or bromide, preferably cetyltrimethylammonium chloride or bromide and $(C_{20}-C_{22})$-alkyl-trimethylammonium chloride or bromide; $(C_{10}-C_{24})$-alkyl-dimethylbenzylammonium chloride or bromide, preferably $(C_{12}-C_{18})$-alkyl-dimethylbenzylammonium chloride; N—$(C_{10}-C_{18})$-alkyl-pyridinium chloride or bromide, preferably N—$(C_{12}-C_{16})$-alkyl-pyridinium chloride or bromide; N—$(C_{10}-C_{18})$-alkyl-isoquinolinium chloride, bromide or monoalkyl sulfate; N—$(C_{12}-C_{18})$-alkyl-polyoylaminoformylmethylpyridinium chloride; N—$(C_{12}-C_{18})$-alkyl-N-methylmorpholinium chloride, bromide or monoalkyl sulfate; N-$(C_{12}-C_{18})$-alkyl-N-ethylmorpholinium chloride, bromide or monoalkyl sulfate; $(C_{16}-C_{18})$-alkyl-pentaoxethylammonium chloride; diisobutylphenoxyethoxyethyldimethylbenzylammonium chloride; salts of N,N-di-ethylaminoethylstearylamide and -oleylamide with hydrochloric acid, acetic acid, lactic acid, citric acid, phosphoric acid; N-acylaminoethyl-N,N-diethyl-N-methyl-ammonium chloride, bromide or monoalkyl sulfate, and N-acylaminoethyl-N,N-diethyl-N-benzylammonium chloride, bromide or monoalkyl sulfate, acyl standing preferably for stearyl or oleyl.

The weight fraction of the cationic surfactants, based on the finished compositions, is preferably from 1 to 10% by weight, more preferably from 2 to 7% by weight, very preferably from 3 to 5% by weight.

Suitable nonionic surfactants include fatty alcohol ethoxylates (alkylpolyethylene glycols); alkylphenol polyethylene glycols; alkylmercaptan polyethylene glycols; fatty amine ethoxylates (alkylaminopolyethylene glycols); fatty acid ethoxylates (acylpolyethylene glycols); polypropylene glycol ethoxylates (Pluronics®); fatty acid alkylol amides, (fatty acid amide polyethylene glycols); N-alkyl-, N-alkoxy-poly-hydroxy-fatty acid amide, sucrose esters; sorbitol esters and polyglycol ethers.

The weight fraction of the nonionic surfactants is preferably from 1 to 20% by weight, more preferably from 2 to 10%, very preferably from 3 to 7% by weight.

Preferred ampho surfactants are N—($C_{12}$–$C_{18}$)-alkyl-β-aminopropionates and N—($C_{12}$–$C_{18}$)-alkyl-β-iminodiproprionates as alkali metal salts and mono-, di-, and trialkylammonium salts; N-acylaminoalkyl-N,N-dimethylacetobetaine, preferably N—($C_8$–$C_{18}$)-acylaminopropyl-N,N-dimethylacetobetaine; ($C_{12}$–$C_{18}$)-alkyl-dimethyl-sulfopropylbetaine; ampho surfactants based on imidazoline (trade name: Miranol®, Steinapon®), preferably the sodium salt of 1-(β-carboxymethyloxyethyl)-1-(carboxymethyl)-2-laurylimidazolinium; amine oxide, e.g., ($C_{12}$–$C_{18}$)-alkyl-dimethyl-amine oxide, fatty acid amidoalkyldimethylamine oxide.

The weight fraction of the amphoteric surfactants is preferably in the range from 0.5 to 20% by weight, more preferably from 1 to 10% by weight.

Particularly preferred surfactants are lauryl sulfate, laureth sulfate, cocoamido-propylbetaine, sodium cocoyl-glutamate, and lauroamphoacetate.

In the compositions of the invention it is additionally possible to employ foam-boosting cosurfactants from the group consisting of alkylbetaines, alkylamido-betaines, aminopropionates, aminoglycinates, imidazolinium betaines, and sulfobetaines, amine oxides and fatty acid alkanol amides or polyhydroxyamides.

As further auxiliaries and additives the compositions of the invention may comprise oily substances, emulsifiers and coemulsifiers, cationic polymers, film formers, and also other additions customary in cosmetology, such as superfatting agents, moisturizing agents, stabilizers, active biogenic substances, glycerol, preservatives, pearlizing agents, dyes and fragrances, solvents, hydrotropic agents, opacifiers, further thickeners and dispersants, and also protein derivatives such as gelatin, collagen hydrolysates, natural or synthetic-based polypeptides, egg yolk, lecithin, lanolin and lanolin derivatives, fatty alcohols, silicones, deodorants, substances with a keratolytic and keratoplastic action, enzymes and carrier substances, antioxidants, UV light protection filters, pigments and metal oxides, and antimicrobial agents.

An oily substance is any fatty substance which is liquid at room temperature (25° C.).

The fatty phase may therefore comprise one or more oils selected preferably from the following oils:

silicone oils, volatile or nonvolatile, linear, branched or cyclic, optionally with organic modification; phenylsilicones; silicone resins and silicone gums; mineral oils such as paraffin oil or vaseline oil; oils of animal origin such as perhydrosqualene, lanolin; oils of plant origin such as liquid triglycerides, e.g., sunflower oil, corn oil, soybean oil, rice oil, jojoba oil, babusscu oil, pumpkin oil, grapeseed oil, sesame oil, walnut oil, apricot oil, macadamia oil, avocado oil, sweet almond oil, lady's-smock oil, castor oil, triglycerides of caprylic/capric acids, olive oil, peanut oil, rapeseed oil, and coconut oil;

synthetic oils such as purcellin oil, isoparaffins, linear and/or branched fatty alcohols and fatty acid esters, preferably guerbet alcohols having 6 to 18, preferably 8 to 10, carbon atoms; esters of linear $C_6$–$C_{13}$ fatty acids with linear $C_6$–$C_{20}$ fatty alcohols; esters of branched $C_6$–$C_{13}$ carboxylic acids with linear $C_6$–$C_{20}$ fatty alcohols, esters of linear $C_6$–$C_{18}$ fatty acids with branched alcohols, especially 2-ethylhexanol; esters of linear and/or branched fatty acids with polyhydric alcohols (such as dimerdiol or trimerdiol, for example) and/or guerbet alcohols; triglycerides based on $C_6$–$C_{10}$ fatty acids;

esters such as dioctyl adipate, diisopropyl dimer dilinoleate; propylene glycols/ dicaprylate or waxes such as beeswax, paraffin wax or microwaxes, alone or in combination with hydrophilic waxes, such as cetylstearyl alcohol, for example; fluorinated and perfluorinated oils; fluorinated silicone oils; mixtures of the aforementioned compounds.

Suitable nonionogenic coemulsifiers include adducts of from 0 to 30 mol of ethylene oxide and/or from 0 to 5 mol of propylene oxide with linear fatty alcohols having 8 to 22 carbon atoms, with fatty acids having 12 to 22 carbon atoms, with alkylphenols having 8 to 15 carbon atoms in the alkyl group, and with sorbitan or sorbitol esters; $C_{12}$–$C_{18}$ fatty acid monoesters and diesters of adducts of from 0 to 30 mol of ethylene oxide with glycerol; glycerol monoesters and diesters and sorbitan monoesters and diesters of saturated and unsaturated fatty acids having 6 to 22 carbon atoms and, where appropriate, their ethylene oxide adducts; adducts of from 15 to 60 mol of ethylene oxide with castor oil and/or hydrogenated castor oil; polyol esters and especially polyglycerol esters, such as polyglyceryl polyricinoleate and polyglyceryl poly-12-phydroxystearate, for example. Likewise suitable are mixtures of compounds from one or more of these classes of substance.

Examples of suitable ionogenic coemulsifiers include anionic emulsifiers, such as mono-, di- or tri-phosphoric esters, but also cationic emulsifiers such as mono-, di-, and tri-alkyl quats and their polymeric derivatives.

Suitable cationic polymers include those known under the INCI designation "Polyquaternium", especially Polyquaternium-31, Polyquaternium-16, Polyquaternium-24, Polyquaternium-7, Polyquaternium-22, Polyquaternium-39, Polyquaternium-28, Polyquaternium-2, Polyquaternium-10, Polyquaternium-11, and also Polyquaternium 37&mineral oil&PPG trideceth (Salcare SC95), PVP-dimethylaminoethyl methacrylate copolymer, guar-hydroxypropyltriammonium chlorides, and also calcium alginate and ammonium alginate. It is additionally possible to employ cationic cellulose derivatives; cationic starch; copolymers of diallylammonium salts and acrylamides; quaternized vinylpyrrolidone/vinylimidazole polymers; condensation products of polyglycols and amines; quaternized collagen polypeptides; quaternized wheat polypeptides; polyethyleneimines; cationic silicone polymers, such as amidomethicones, for example; copolymers of adipic acid and dimethylaminohydroxypropyidiethylenetriamine; polyaminopolyamide and cationic chitin derivatives, such as chitosan, for example.

Examples of suitable silicone compounds are dimethylpolysiloxane, methylphenylpolysiloxanes, cyclic silicones, and amino-, fatty acid-, alcohol-, polyether-, epoxy-, fluoro- and/or alkyl-modified silicone compounds, and also polyalkylsiloxanes, polyalkylarylsiloxanes, polyethersiloxanes, as described in U.S. Pat. No. 5,104,645 and the documents cited therein, which at room temperature may be present either in liquid form or in resin form.

Suitable film formers, depending on the intended application, include salts of phenylbenzimidazolesulfonic acid, water-soluble polyurethanes, for example, $C_{10}$-polycarbamyl, polyglycerol esters, polyvinyl alcohol, polyvinylpyrrolidone, copolymers thereof, for example vinylpyrrolidone/vinyl acetate copolymer, water-soluble acrylic acid polymers/copolymers and their esters or salts, examples being partial ester copolymers of acrylic/methacrylic acid and polyethylene glycol ethers of fatty alcohols, such as acrylate/steareth-20 methacrylate copolymer, water-soluble cellulose, examples being hydroxymethylcellulose, hydroxyethylcellulose, hydroxypropylcellulose, water-soluble quaterniums, polyquaterniums, carboxyvinyl polymers, such as carbomers and their salts, polysaccharides, polydextrose for example, and glucan.

As superfatting agents it is possible to use substances such as, for example, polyethoxylated lanolin derivatives, lecithin derivatives, polyol fatty acid esters, monoglycerides, and fatty acid alkanol amides, the latter serving simultaneously as foam stabilizers. Moisturizers available include for example isopropyl palmitate, glycerol and/or sorbitol.

As stabilizers it is possible to use metal salts of fatty acids, such as magnesium, aluminum and/or zinc stearate, for example.

Active biogenic substances are to be understood as including, for example, plant extracts and vitamin complexes.

Additionally, the compositions of the invention may comprise organic solvents. Suitable organic solvents include in principle all monohydric or polyhydric alcohols. Preference is given to using alcohols having 1 to 4 carbon atoms such as ethanol, propanol, isopropanol, n-butanol, isobutanol, t-butanol, glycerol, and mixtures of said alcohols. Further preferred alcohols are polyethylene glycols having a relative molecular mass of less than 2 000. Particular preference is given to the use of polyethylene glycol having a relative molecular mass of between 200 and 600 in amounts of up to 45% by weight and of polyethylene glycol having a relative molecular mass of between 400 and 600 in amounts of from 5 to 25% by weight. Further suitable solvents are, for example, triacetin (glyceryl triacetate) and 1-methoxy-2-propanol. A hydrotropic action is developed by short-chain anionic surfactants, especially arylsulfonates, for example, cumene sulfonate or toluene sulfonate.

The compositions of the invention can be blended with conventional ceramides, pseudoceramides, fatty acid N-alkylpolyhydroxyalkyl amides, cholesterol, cholesterol fatty acid esters, fatty acids, triglycerides, cerebrosides, phospholipids, and similar substances as a care additive.

Examples of suitable preservatives include phenoxyethanol, parabens, pentanediol or sorbic acid.

As dyes it is possible to use the substances which are suitable and approved for cosmetic purposes.

Suitable active antifungal substances (fungicides) include preferably ketoconazole, oxiconazole, bifonazole, butoconazole, cloconazole, clotrimazole, econazole, enilconazole, fenticonazole, isoconazole, miconazole, sulconazole, tioconazole, fluconazole, itraconazole, terconazole, naftifine and terbinafine, Zn pyrithione, and octopirox.

In one preferred embodiment the compositions are rinse-off products, more preferably shampoos, shower baths, shower gels, and foam baths. Modern rinse-off products frequently have a high proportion of active conditioning substances, which may also be in the form of oily fractions. Consequently, these compositions may be present as emulsions.

In another preferred embodiment the compositions are leave-on products, preferably in the form of emulsions, more preferably skincare agents, day creams, night creams, beauty creams, nutrient creams, body lotions, ointments, sun protection compositions, lipcare compositions, and deodorants.

They are also suitable, furthermore, for surfactant-free aqueous compositions and emulsions, for example, for hair cures and hair rinses, hair gels, and also permanent waving compositions, hair-coloring compositions, and for decorative cosmetics, examples being makeups, eye shadows, lipsticks, mascara, and the like.

A key point of the invention is that the compositions of the invention can be used even in the absence of an additional coemulsifier and/or bodying agent. The additional use of coemulsifiers and/or bodying agents is accordingly not mandatory, although naturally it is possible. Combination with other known coemulsifiers and/or bodying agents may be desirable in order to set specific cosmetic profiles and to exploit synergistic effects.

The nature of the compositions is extremely advantageous:

Accordingly, emulsions of the invention are creamy and ointment-like and above all do not have the gel-like or even gelatine-like appearance of prior art emulsions in which the external aqueous phase is thickened. The cosmetic feel on the skin is outstanding; upon application to the skin the emulsions impart a sensation of freshness and of comfort, and at the same time have a rich and nourishing effect; moreover, they are very soft and luxurious and in no way sticky.

The examples which follow serve to illustrate the invention, though without restricting it (all percentages are by weight). The copolymers used in the examples are representatives of the particularly preferred copolymers 1 to 67 already listed in the description. They were prepared by the therein-indicated processes 1, 2, 3 or 4 using the preferred initiators and solvents.

EXAMPLE 1

O/W Skin Milk with Keratolytic Effect

| | Composition | |
|---|---|---|
| A | Copolymer No. 64 | 1.50% |
| | Mineral oil | 4.00% |
| | Almond oil | 4.00% |
| | ®Cetiol SN (Henkel) | 8.00% |
| | Cetearyl isononanoate | |
| | Cetyl alcohol | 2.00% |
| | Stearic acid | 2.00% |
| B | ®Aristoflex AVC (Clariant) | 0.30% |
| | Ammonium acryloyldimethyltaurate-VP copolymer | |
| C | Water | ad 100% |
| | Citric acid | 0.30% |
| | Malic acid | 0.40% |
| | Glycolic acid | 0.70% |
| | Lactic acid | 0.70% |
| D | Fragrances | 0.30% |

Preparation
I Mix A and B.
II Mix the components C.
III Add II to I.
II Stir D into I.
III Homogenize emulsion, pH 3.5.

EXAMPLE 2

O/W Skin Milk for Dry Skin

| | Composition | |
|---|---|---|
| A | ®EMULSOGEN SRO (Clariant) | 1.00% |
| | Rapeseed oil sorbitol ester | |
| | Mineral oil, perliquidum | 5.00% |
| | Isopropyl palmitate | 6.00% |
| | Jojoba oil | 2.00% |
| | Caprylic/capric triglyceride | 4.00% |
| | Soybean oil | 3.00% |
| B | Copolymer No. 18 | 1.00% |
| C | ®HOSTAPON CLG (Clariant) | 0.60% |
| | Sodium lauroyl glutamate | |
| | ®AQUAMOLLIN BC Powd. high-conc. (Clariant) | 0.10% |
| | Ethylenediaminetetraacetate, Na salt | |
| | Citric acid (10% aqueous) | 2.00% |
| | Glycerol | 3.00% |
| | Water | ad 100% |
| | Preservative | q.s. |
| D | Fragrance | 0.30% |

Preparation:
I Mix A and B.
II Stir solution of C into I.
III Add D to II.
IV Homogenize emulsion.
V Adjust pH to 4.8.

EXAMPLE 3

W/O Emulsion: Depigmenting Cream

| | Composition | |
|---|---|---|
| A | ®HOSTACERIN DGI (Clariant) | 4.00% |
| | Polyglyceryl-2 sesquiisostearate | |
| | Cetyl alcohol | 1.20% |
| | Stearic acid | 1.00% |
| | ®Cetiol V (Henkel KGaA) | 5.00% |
| | Decyl oleate | |
| | Beeswax | 2.00% |
| | Cyclomethicone | 7.00% |
| B | Copolymer No. 32 | 1.5% |
| | Kojic acid | 1.00% |
| | Caffeic acid | 1.00% |
| | Water | ad 100% |
| C | PEG 600 (Clariant) | 10.00% |
| | PEG-12 | |
| | Preservative | q.s. |
| D | Fragrance | 0.40% |

Preparation:
I Melt A at 80° C.
II Stir B into I.
III Cool with stirring.
IV At 35° C., add C to IV.
V pH 3.4.
W/O emulsion.

EXAMPLE 4

W/O Cream

| | Composition | |
|---|---|---|
| A | ®HOSTACERIN WO (Clariant) | 10.00% |
| | Polyglyceryl-2 sesquiisostearate, cera alba (beeswax), cera microcrystallina (microcrystalline wax), mineral oil, magnesium stearate, aluminum stearates | |
| | ®Permulgin 3510 (Henkel KGaA) | 4.00% |
| | Cera alba (beeswax), petrolatum | |
| | Copolymer No. 10 | 1.5% |
| | Isopropyl palmitate | 7.00% |
| | Shea butter | 2.00% |
| | Walnut oil | 7.00% |
| | Vaseline | 7.00% |
| | ®Cetiol V (Henkel KGaA) | 5.00% |
| | Decyl oleate | |
| B | 1,2-Propylene glycol | 3.00% |
| | Water | ad 100% |
| | Citric acid | 0.30% |
| | Malic acid | 0.40% |
| | Glycolic acid | 0.70% |
| | Lactic acid | 0.70% |
| | Preservative | q.s. |
| C | Fragrance | 0.40% |

Preparation
I Melt A at 80° C.
II Heat B to 80° C.
III Stir II into I.
IV Cool with stirring.
V At 35° C., add C to IV.
VI pH about 4.5.

EXAMPLE 5

Spray Emulsion

| | Composition | |
|---|---|---|
| A | ®EMULSOGEN SRO (Clariant) | 4.00% |
| | Rapeseed oil sorbitol ester | |
| | Caprylic/capric triglyceride | 1.00% |
| | Cetearyl isononanoate | 0.50% |
| | Mineral oil l.v. | 0.50% |
| | Isopropyl palmitate | 0.50% |
| | Cetearyl alcohol | 0.50% |
| B | Copolymer No. 13 | 0.20% |
| C | Water | ad 100% |
| | Citric acid | 3.00% |
| | Preservative | q.s. |
| D | Water | 37.00% |
| | ®HOSTAPON CLG (Clariant) | 0.60% |
| | Sodium lauroyl glutamate | |
| | Glycerol | 5.00% |
| | Panthenol | 0.50% |
| E | Tocopherol acetate | 0.20% |
| | Alcohol | 4.00% |

Preparation
I Melt A at about 70° C.
II Add B to I.
III Heat C to about 70° C.
IV Preparation of the W/O emulsion: stir III into I at high speed (for about 2 min).
V Stir solution of D into IV at room temperature and cool with stirring (at least 2 h).
VI Add E to V.
VII Adjust pH to 4.8.

Examples of surfactant formulations

EXAMPLE 6

Clear Shower Bath Having Good Foaming Properties

| | Composition | |
|---|---|---|
| A | ®GENAPOL LRO liquid (Clariant) | 40.00% |
| | Sodium laureth sulfate | |
| B | Fragrance | 0.30% |
| C | Water | ad 100% |
| | Dye | q.s. |
| | Preservative | q.s. |
| | ®GENAGEN LDA (Clariant) | 6.00% |
| | Disodium lauroamphodiacetate | |
| | Citric acid | 5.00% |
| D | Copolymer No. 37 | 1.50% |

Preparation
I Stir B into A.
II Add components from C successively to I.
III Adjust pH to about 5.0.
IV Adjust the viscosity by stirring D into II.

EXAMPLE 7

Antidandruff Shampoo, Clear

| | Composition | |
|---|---|---|
| A | ®OCTOPIROX (Clariant) | 0.50% |
| | Piroctone olamine | |
| B | Water | 10.00% |
| C | ®GENAPOL LRO liq. (Clariant) | 30.00% |
| | Sodium laureth sulfate | |
| D | ®Belsil DMC 6032 (Wacker Chemie) | 1.50% |
| | Dimethicone copolyol acetate | |
| | Fragrance | 0.30% |
| E | ®ALLANTOIN (Clariant) | 0.30% |
| F | Water | 46.40% |
| G | Dye | q.s. |
| | Panthenol (Hoffmann La Roche) | 1.00% |
| | ®GENAGEN CAB (Clariant) | 8.00% |
| | Cocamidopropylbetaine | |
| H | Copolymer No. 49 | 1.10% |
| | Citric acid | 3.00% |

Preparation
I Mix A with B.
II Stir C into I until clear solution is obtained.
III Add components from D successively to I.
IV Stir E into F with heating and then stir mixture into I.
V Add components from G successively to I.
VII Adjust the viscosity by stirring H into I.
IIX pH about 4.5.

EXAMPLE 8

Anti-aging Gel

| A | Glycerol | 3.00% |
|---|---|---|
| | Water | ad 100% |
| | Citric acid | 0.30% |
| | Malic acid | 0.40% |
| | Glycolic acid | 0.70% |
| | Lactic acid | 0.70% |
| | Preservative | q.s. |
| B | Fragrance | 0.30% |
| C | Copolymer No. 56 | 1.50% |

Preparation
I Mix A and B.
II Add C to I.
III Adjust pH to 5.0.

EXAMPLE 9

Clear Refreshing Gel, Moisturizing

| A | Glycerol | 3.00% |
|---|---|---|
| | Ethanol | 20.00% |
| | Water | ad 100% |
| | Preservative | q.s. |
| B | Fragrance | 0.30% |
| C | Copolymer No. 20 | 1.50% |

Preparation
I Mix A and B.
II Add C to I.
V Adjust pH to 6.0

EXAMPLE 10

Gel with Keratolytic Effect

| A | Water | ad 100% |
|---|---|---|
| | Glycerol | 3.00% |
| | 3,6,9-Trioxaundecanedioic acid | 4.00% |
| | Preservative | q.s. |
| | Fragrance | 0.30% |
| | Copolymer No. 25 | 1.50% |

Preparation
I Mix components successively.
II Adjust pH to 3.8.

What is claimed is:

1. An acidic cosmetic, dermatological or pharmaceutical liquid or gel composition which comprises an inorganic or groan ic acid and at least one copolymer obtained by free-radical copolymerization of
   A) acryloyldimethyltaurine or acryloyldimethyltaurates, and mixtures thereof,
   B) optionally, one or more further olefinically unsaturated, noncationic, comonomers which have at least one oxygen, nitrogen, sulfur or phosphorus atom and possess a molecular weight of less than 500 g/mol,
   C) optionally, one or more olefinically unsaturated, cationic comonomers which have at least one oxygen, nitrogen, sulfur or phosphorus atom and possess a molecular weight of less than 500 g/mol,
   D) one or more silicon-containing components capable of free-radical polymerization and having a functionality of at least one, E) optionally, one or more fluorine-containing components capable of free-radical polymerization and having a functionality of at least one, F) optionally, one or more olefinically mono- or polyunsaturated, macromonomers each possessing at least one oxygen, nitrogen, sulfur or phosphorus atom and having a number-average molecular weight of greater then or equal to 200 g/mol, the macromonomers not being a silicon-containing component D) or fluorine-containing component E), and where at least one macr6monomer is a macromonomer of formula (IV)

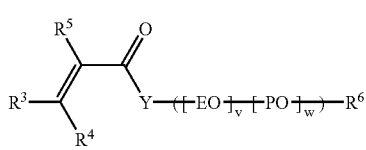

(IV)

in which $R_3$, $R_4$, $R_5$, and $R_6$ independently of one another are hydrogen or n-aliphatic, iso-aliphatic. olefinic, cycloaliphatic, arylaliphatic or aromatic ($C_1$–$C_{30}$) hydrocarbon radicals, v and w independently of one another are from 0 to 500, the sum of v and w is on average $\geq 1$, and Y is selected from the group consisting of —O—, —C(O)—, —C(O)—O—, —S—, —O—$CH_2$—CH(O—)—$CH_2OH$, —O—$CH_2$—CH(OH)—$CH_2O$—, —O—$SO_2$—O—, —O—$SO_2$—O—, —O—SO—O—, —PH—, —P($CH_3$)—, —$PO_3$—, —NH—, and —N($CH_3$)—, G) optionally, the copolymerization taking place in the presence of at least one polymeric additive having number-average molecular weights of from 200 g/mol to $10^9$ g/mol, H) with the proviso that component A) is copolymerized with at least one component selected from one of the components D) to G), and wherein said acid ranges from 0.05 to 20 weight percent of said composition.

2. The acidic composition as claimed in claim 1, wherein the comonomers B) are selected from the group consisting of unsaturated carboxylic acids, salts of unsaturated carboxylic acids, anhydrides of unsaturated carboxylic acids, esters of unsaturated carboxylic acids with aliphatic, olefinic, cycloaliphatic, arylaliphatic or aromatic alcohols having 1 to 22 carbon atoms, open-chain N-vinyl amides, cyclic N-vinyl amides having a ring size of from 3 to 9, amides of acrylic acid, amides of methacrylic acid, amides of substituted acrylic acids, amides of substituted methacrylic acids, 2-vinylpyridine, 4-vinylpyridine, vinyl acetate; styrene, acrylonitrile, vinyl chloride, vinylidene chloride, tetrafluoroethylene, vinylphosphonic acid or the esters or salts thereof, vinylsulfonic acid or the esters or salts thereof, allylphosphonic acid or the esters or salts thereof, methallylsulfonic acid or the esters or salts thereof, and mixtures thereof.

3. The acidic composition as claimed in claim 1, wherein the comonomers C) are selected from the group consisting of diallyldimethylammonium chloride (DADMAC),

[2-(methacryloyloxy)ethyl]trimethylammonium chloride (MAPTAC),

[2-(acryloyloxy)ethyl]trimethylammonium chloride,

[2-methacrylamidoethyl]trimethylammonium chloride,

[2-(acrylamido)ethyl]trimethylammonium chloride,

N-methyl-2-vinylpyridinium chloride,
N-methyl-4-vinylpyridinium chloride,
dimethylaminoethyl methacrylate,
dimethylaminopropylmethacrylamide,
methacryloylethyl N-oxide,
methacryloylethylbetaine, and mixtures thereof.

4. The acidic composition as claimed claim 1, wherein said silicon-containing components D) are compounds of the formula (I)

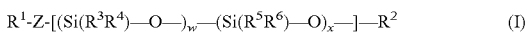

(I)

where $R^1$ represents a polymerizable function from a vinylically unsaturated compound;

Z is a chemical bridge, $R^3$, $R^4$, $R^5$, and $R^6$ independently of one another are —$CH_3$, —O—$CH_3$, —$C_6H_5$ or —O—$C_6H_5$;

w and x denote numbers from 0 to 500, it being necessary for either w or x to be greater than zero; and $R^2$ is a saturated or unsaturated aliphatic, cycloaliphatic, arylaliphatic or aromatic radical having in each case 1 to 50 carbon atoms or a group of the formulae —OH, —$NH_2$, —N($CH_3$)$_2$, —$R^7$ or a group -Z-$R^1$, where Z and $R^1$ have the meanings mentioned above, $R^1$ and $R^7$ is selected from the group consisting of the formula —O—Si($CH_3$)$_3$, —O—Si(phenyl)$_3$, —O—Si(O—Si($CH_3$)$_3$)$_2$$CH_3$) and —O—Si(O—Si(phenyl)$_3$)$_2$phenyl).

5. The acidic composition of claim 1, wherein the fluorine-containing components E) are compounds of the formula (II)

(II)

where $R^1$ is a polymerizable function from vinylically unsaturated compounds;

Y is a chemical bridge, and r, s are stoichiometric coefficients which independently of one another denote numbers from 0 to 200.

6. The acidic composition of claim 1, wherein component F) further comprises one or more of the formula (III)

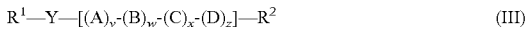

(III)

where $R^1$ represents a polymerizable function from a vinylically unsaturated compound;

Y is a chemical bridge,

A, B, C, and D independently of one another are discrete chemical repeating units;

v, w, x, and z independently of one another amount to from 0 to 500, the sum of v, w, x, and z being on average $\geq 1$; and $R^2$ is a linear or branched aliphatic, olefinic, cycloaliphatic, arylaliphatic or aromatic ($C_1$–$C_{50}$) hydrocarbon radical, OH, —$NH_2$ or —N($CH_3$)$_2$ or is [—Y—$R^1$].

7. The acidic composition of claim 1, wherein the polymeric additive G) is selected from the group consisting of a polyalkylene glycol, an alkylpolyglycol and mixtures thereof or a homopolymer or copolymer of a compound selected from the group consisting of N-vinylformamide, N-vinylacetamide, N-vinylpyrrolidone, ethylene oxide. propylene oxide, acryloyldimethyltaurine, N-vinylcaprolactone, N-vinylmethylacetamide, acrylamide, acrylic acid, methacrylic acid, N-vinylmorpholide, hydroxymethyl methacrylate, diallyldimethylammonium chloride (DADMAC), [2-(methacryloyloxy)ethyl]trimethylammonium chloride (MAPTAC), and mixtures thereof.

8. The acidic composition of claim 1, wherein the copolymerization takes place in the presence of at least one polymeric additive G).

9. The acidic composition of claim 1, wherein the copolymer is crosslinked.

10. The acidic composition of claim 1, wherein the copolymer is prepared by precipitation polymerization in tert-butanol.

11. The acidic composition of claim 1, wherein the copolymer is water-soluble or water-swellable.

12. The acidic composition of claim 1, which comprises, based on the finished composition, from 0.01 to 10% by weight of the copolymer.

13. The acidic composition of claim 1, which possesses a pH of less than or equal to 6.5.

14. The acidic composition of claim 13, which possesses a pH in the range from 2 to 6.5.

15. An acidic cosmetic, dermatological or pharmaceutical liquid or gel composition which comprises an inorganic or organic acid and at least one copolymer obtained by free-radical copolymerization of
A) acryloyldimethyltaurine or acryloyldimethyltaurates, and mixtures thereof,
B) optionally, one or more further olefinically unsaturated, noncationic, comonomers which have at least one oxygen, nitrogen, sulfur or phosphorus atom and possess a molecular weight of less than 500 g/mol,
C) optionally, one or more olefinically unsaturated, cationic comonomers which have at least one oxygen, nitrogen, sulfur or phosohorus atom and possess a molecular weight of less than 500 g/mol,
D) one or more silicon-containing components capable of free-radical polymerization and having a functionality of at least one,
E) optionally, one or more fluorine-containing components capable of free-radical polymerization and having a functionality of at least one,
F) optionally, one or more olefinically mono- or polyunsaturated, macromonomers each possessing at least one oxygen, nitrogen, sulfur or phosphorus atom and having a number-average molecular weight of greater than or equal to 200 g/mol, the macromonomers not being a silicon-containing component D) or fluorine-containing component E), and where at least one macromonomer is a macromonomer of formula (IV)

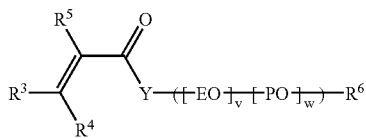

(IV)

in which
R$_3$, R$_4$, R$_5$, and R$_6$ independently of one another are hydrogen or n-aliphatic, iso-aliphatic, olefinic, cycloaliphatic, arylaliphatic or aromatic (C$_1$–C$_{30}$) hydrocarbon radicals,
v and w independently of one another are from 0 to 500, the sum of v and w is on average $\geq 1$, and Y is selected from the group consisting of —O—, —C(O)—, —C(O)—O—, —S—, —O—CH$_2$—CH(O—)—CH$_2$OH, —O—CH$_2$—CH(OH)—CH$_2$O—, —O—SO$_2$—O—, —O—SO$_2$—O—SO—O—, —PH—, —P(CH$_3$)—, —PO$_3$—, —NH—, and —N(CH$_3$)—,
G) optionally, the copolymerization taking place in the presence of at least one polymeric additive having number-average molecular weights of from 200 g/mol to 10$^9$ g/mol,
H) with the proviso that component A) is copolymerized with at least one component selected from one of the components D) to G), and wherein said acid ranges from 0.05 to 20 weight percent of said composition
wherein said acid is i) an alpha-hydroxy acid or ii) an acid selected from the group consisting of glycolic acid, lactic acid, citric acid, tartaric acid, mandelic acid, salicylic acid, ascorbic acid, pyruvic acid, oligooxa-monocarboxylic and -dicarboxylic acids, fumaric acid, retinoic acid, aliphatic and organic sulfonic acid, benzoic acid, kojic acid, fruit acid, malic acid, gluconic acid, galacturonic acid, and mixtures thereof, or iii) a compound selected from the group consisting of an acidic plant extract, a fruit extract, a fruit extract derivative, an acid plant extract derivative, and mixtures thereof, or a mixture of i), ii) and iii).

16. The acidic composition of claim 1, which is in the form of an emulsion, aqueous gel or surfactant-containing formulation.

17. The acidic composition of claim 1, which is in the form of a rinse-off composition.

18. The acidic composition of claim 1, which is in the form of a leave-on composition.

19. The acidic composition of claim 4 wherein the chemical bridge Z is selected from the group consisting of —O—, —((C$_1$–C$_{50}$)alkylene)-, —((C$_6$–C$_{30}$)arylene)-, —((C$_5$–C$_8$)cycloalkylene)-, —((C$_1$–C$_{50}$)alkenylene)-, -(polypropylene oxide)$_n$-, -(polyethylene oxide)$_o$-, -(polypropylene oxide)$_n$-(polyethylene oxide)$_o$-, and mixtures thereof, where n and a independently of one another denote numbers from 0 to 200 and the distribution of EO/PO units can be random or in block form, and/or selected from the group consisting of —((C$_1$–C$_{10}$)alkyl)-(Si(OCH$_3$)$_2$)— and —(Si(OCH$_3$)$_2$)—.

20. The acidic composition of claim 4 wherein, R$^1$ is a radical selected from the group consisting of vinyl, allyl, methallyl, methylvinyl, acryloyl methacryloyl, crotonyl, senecionyl, itaconyl, maleyl, fumaryl, styryl, and mixtures thereof.

21. The acidic composition of claim 5 wherein, R$^1$ is a radical selected from the group consisting of vinyl, allyl, methallyl, methylvinyl, acryloyl, methacryloyl, crotonyl, senecionyl, itaconyl, maleyl, fumaryl, styryl, and mixtures thereof.

22. The acidic composition of claim 6 wherein, R$^1$ is a radical selected from the group consisting of vinyl, allyl, methallyl, methylvinyl, acryloyl, methacryloyl, crotonyl, senecionyl, itaconyl, maleyl, fumaryl, styryl, and mixtures thereof.

23. The acidic composition of claim 5, wherein the chemical bridge Y is selected from the group consisting of —O—, —C(O)—, —C(O)—O—, —S—, —O—CH$_2$—CH(O—)—CH$_2$OH, —O—CH$_2$—CH(OH)—CH$_2$—O—, —O—SO$_2$—O—, —O—S(O)—O—, —PH—, —P(CH$_3$)—, —PO$_3$—, —NH—, —N(CH$_3$)—, —O—(C$_1$–C$_{50}$)alkyl-O—, —O -phenyl-O—, —O-benzyl-O—, —O—(C$_5$–C$_8$)cycloalkyl-O—, —O—(C$_1$–C$_{50}$)alkenyl-O—, —O—(CH(CH$_3$)—CH$_2$—O)$_n$—, —O—(CH$_2$—CH$_2$O)$_n$—, —O—([CH—CH$_2$—O]$_n$—[CH$_2$—CH$_2$—O]$_m$)$_o$—, where n, m, and o independently of one another denote numbers from 0 to 200, and mixtures thereof.

24. The acidic composition of claim 6, wherein Y is a bridging group selected from the group consisting of —O—, —S—, —C(O)—, —C(O)—O—, —O—CH₂—CH(O—)—CH₂OH, —O—CH₂—CH(OH)—CH₂O—, —O—SO₂—O—, —O—SO—O—, —PH—, —P(CH₃)—, —PO₃—, —NH—, —N(CH₃)—, and mixtures thereof.

25. The acidic composition of claim 6 wherein the discrete repeating units of A, B, C, and D are originating from a unit selected from the group consisting of acrylamide, methacrylamide, ethylene oxide, propylene oxide, AMPS, acrylic acid, methacrylic acid, methyl methacrylate, acrylonitrile, maleic acid, vinyl acetate, styrene, 1,3-butadiene, isoprene, isobutene, diethylacrylamide, diisopropylacrylamide, and mixtures thereof.

26. The acidic composition of claim 6 wherein the discrete repeating units of A, B, C, and D are originating from a unit of ethylene oxide or propylene oxide.

27. The acidic composition of claim 6, wherein v, w, x, and z independently of one another amount to from 1 to 30.

28. The acidic composition of claim 15, which contains from 0.5 to 10% by weight of said acid.

29. A liquid or gel acidic cosmetic, dermatological or pharmaceutical composition which comprises from 0.05 to 20 weight percent of an organic or inorganic acid end at least one copolymer obtained by free-radical copolymerization of acryloyldimethyltaurine or acryloyldimethyltaurates, or mixtures thereof, with at least one component selected from the group consisting of:
a) one or more silicon-containing component (D) capable of free-radical polymerization and having a functionality of at least one,
b) one or more fluorine-containing component (E) capable of free-radical polymerization and having a functionality of at least one,
c) one or more olefinically mono- or polyunsaturated, macromonomer (F) (each possessing at least one oxygen, nitrogen, sulfur or phosphorus atom and having a number-average molecular weight of greater than or equal to 200 g/mol, the macromonomer not being the silicon-containing component a) or the fluorine-containing component b), and where at least one macromonomer is a macromonomer of formula (IV)

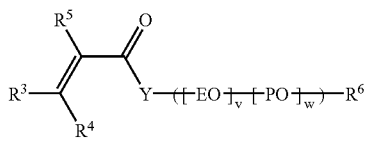

in which $R_3$, $R_4$, $R_5$, and $R_8$ independently of one another are hydrogen or n-aliphatic, iso-aliphatic, olefinic, cycloaliphatic, arylaliphatic or aromatic ($C_1$–$C_{30}$) hydrocarbon radicals, v and w independently of one another are from 0 to 500, the sum of v and w is on average $\geq 1$, and Y is selected from the group consisting of —O—, —C(O)—, —C(O)—O—, —S—, —O—CH₂—CH(O—)—CH₂OH, —O—CH₂—CH(OH)—CH₂O—, —O—SO₂—O—, —O—SO—O—, —PH—, —P(CH₃)—, —PO₃—, —NH—, and —N(CH₃)—, and d) at least one polymeric additive (G) having number-average molecular weights of from 200 g/mol to $10^9$ g/mol, e) one or more further olefinically unsaturated, noncationic comonomer (B) which have at least one oxygen, nitrogen, sulfur or phosphorous atom and possess a molecular weight of less than 500 g/mol, f) one or more olefinically unsaturated, cationic comonomer (C) which has at least one oxygen, nitrogen, sulfur or phosphorus atom and possess a molecular weight of less than 500 g/mol, with the proviso that when component B or C is copolymerized, at least one further component is selected from the group consisting of components D, E, F, and G.

30. The liquid or gel acidic cosmetic, dermatological or pharmaceutical composition of claim 29, wherein said macromonomer c) is crosslinking.

31. The liquid or gel acidic cosmetic, dermatological or pharmaceutical composition of claim 29, wherein said olefinically unsaturated, noncationic comonomer e) is crosslinking.

32. The liquid or gel acidic cosmetic, dermatological or pharmaceutical composition of claim 29, wherein the at least one copolymer is obtained by the free-radical polymerization of acryloyldimethyltaurine or acryloyldimethyltaurates, or mixtures thereof (A) and the at least one component is selected from the group consisting of component (F); component (D); component (E); components (C) and (D); components (C) and (E); and components (D) and (F).

33. The liquid or gel acidic cosmetic, dermatological or pharmaceutical composition of claim 32, wherein the at least one copolymer is obtained by the free-radical polymerization in the absence of (G).

34. The liquid or gel acidic cosmetic, dermatological or pharmaceutical composition of claim 32, wherein the at least one copolymer is obtained by the free-radical polymerization in the presence of (G).

35. The liquid or gel acidic cosmetic, dermatological or pharmaceutical composition of claim 29, wherein said composition comprises from 0.5 to 20 weight percent of the organic or inorganic acid.

36. The liquid or gel acidic cosmetic, dermatological or pharmaceutical composition of claim 29, wherein the organic acid is i) an alpha-hydroxy acid or ii) an acid selected from the group consisting of glycolic acid, lactic acid, citric acid, tartaric acid, mandelic acid, salicylic acid, ascorbic acid, pyruvic acid, oligooxa-monocarboxylic and -dicarboxylic acids, fumaric acid, retinoic acid, aliphatic and organic sulfonic acid, benzoic acid, kojic acid, fruit acid, malic acid, gluconic acid, galacturonic acid, and mixtures thereof, or iii) a compound selected from the group consisting of an acidic plant extract, a fruit extract, a fruit extract derivative, an acid plant extract derivative, and mixtures thereof or a mixture of i), ii) and iii).

* * * * *